US009278992B2

(12) United States Patent
Makishima et al.

(10) Patent No.: US 9,278,992 B2
(45) Date of Patent: Mar. 8, 2016

(54) FUNCTION-SELECTIVE VITAMIN D RECEPTOR AGONIST (75) Inventors: Makoto Makishima, Tokyo (JP);
Michiyasu Ishizawa, Tokyo (JP);
Manabu Matsunawa, Tokyo (JP);
Sachiko Yamada, Tokyo (JP)

(73) Assignee: Nihon University, Tokyo (JP)

( * ) Notice: Subject to any disclaimer, the term of this patent is extended or adjusted under 35 U.S.C. 154(b) by 767 days.

(21) Appl. No.: 12/601,998

(22) PCT Filed: Jan. 7, 2008

(86) PCT No.: PCT/JP2008/050027
§ 371 (c)(1),
(2), (4) Date: Apr. 15, 2010

(87) PCT Pub. No.: WO2008/149563
PCT Pub. Date: Dec. 11, 2008

(65) Prior Publication Data
US 2010/0204191 A1    Aug. 12, 2010

(30) Foreign Application Priority Data

Jun. 4, 2007 (JP) ................................. 2007-147866

(51) Int. Cl.
C07J 9/00        (2006.01)
A61K 31/56       (2006.01)
A61K 31/575      (2006.01)

(52) U.S. Cl.
CPC . C07J 9/00 (2013.01); A61K 31/575 (2013.01)

(58) Field of Classification Search
USPC .............................. 514/182; 552/555; 435/375
See application file for complete search history.

(56) References Cited

U.S. PATENT DOCUMENTS 3,846,411 A * 11/1974 Widauer et al. ............... 540/112

OTHER PUBLICATIONS

Kozoni et al. (Oxford Journals, Life Science and Medicine Carcinogenesis, (2000), vol. 21, issue 5, pp. 999-1005).*
Adachi et al. (J Lipid Res. Jan. 2005; 46(1):46-57, Epub Oct. 16, 2004).*
Jurutka at el ( J Cell Biochem. Apr. 1, 2005;94(5):917-43).*
Makoto Makishima et al Science May 17, 2002: vol. 296 No. 5571 pp. 1313-1316.*
Shaikh et al., "Synthesis and mesomorphic behavior of lithocholic acid derivatives", Bulletin of Material Science, 2003, vol. 26, No. 5, p. 559-563.
Adachi, R. et al., "Selective activation of vitamin D receptor by lithocholic acid acetate, a bile acid derivative", Journal of Lipid Research, 2005, vol. 46, p. 46-57.
Nagpal, S. et al., "Noncalcemic actions of vitamin D receptor ligands", Endocrine Reviews, 2005, vol. 26, No. 5, p. 662-687.
Makishima M. et al., "Vitamin D Receptor as an Intestinal bile acid sensor", Science, May 17, 2002, vol. 296, p. 1313-1316.
Ishizawa, M. et al., "Lithocholic acid derivatives act as selective vitamin D receptor modulators", J Lipid Res, Jan. 7, 2008.
International preliminary examination report on patentability for corresponding PCT application PCT/JP2008/050027.

* cited by examiner

Primary Examiner — Sabiha N Qazi
(74) Attorney, Agent, or Firm — Morgan, Lewis & Bockius LLP (57) ABSTRACT The present invention provides a VDR ligand which does not induce hypercalcemia that is an adverse reaction of a vitamin D3 preparation; and a composition which comprises lithocholic acid propionate, a salt thereof, a solvate thereof, or a prodrug thereof.

15 Claims, 5 Drawing Sheets

FUNCTION-SELECTIVE VITAMIN D RECEPTOR AGONIST

CROSS-REFERENCE TO THE RELATED APPLICATIONS

This application is a national stage of international application No. PCT/JP2008/050027, filed Jan. 7, 2008, and claims benefit of priority under 35 USC 119 to Japanese Patent Application No. 2007-147866, filed on Jun. 4, 2007, the entire contents of which are incorporated herein by reference.

TECHNICAL FIELD

The present invention relates to a function-selective vitamin D receptor agonist.

BACKGROUND ART

The active form of vitamin D3 regulates the in vivo calcium and phosphoric acid metabolisms as well as bone metabolism through a vitamin D receptor (VDR). Vitamin D deficiency causes rachitis and osteomalacia, and the active form of vitamin D3 and its derivatives are used as therapeutic agents for these diseases. Vitamin D derivatives are used as therapeutic agents for osteoporosis in the form of oral medicines, and as therapeutic agents for psoriasis vulgaris in the form of topical agents.

The vitamin D derivatives are reported to have effects of inhibiting the growth and inducing the differentiation of malignancies (myeloid leukemia, breast cancer, prostate cancer, colon cancer, etc.), an immunomodulatory effect (therapeutic efficacy on autoimmune disease models), and a natural immunity-enhancing effect (antituberculous activity) (Non-Patent Document 1).

However, when a vitamin D derivative is administered to an animal, the effect (adverse drug reaction) of elevating blood calcium levels was difficult to be separated from other VDR-mediated actions.

Lithocholic acid, which is a bile acid, has also been verified to function as a VDR ligand (Non-Patent Document 2). Lithocholic acid acetate, which is a lithocholic acid derivative, is reported to have more potency on VDR than lithocholic acid (Non-Patent Document 3). Lithocholic acid acetate induced the differentiation of leukemic cells.

In addition to VDR, lithocholic acid also has effects of activating farnesoid X receptor (FXR) and G protein-coupled bile acid receptor 1 (GPBAR1) (Non-Patent Documents 4 and 5). Lithocholic acid acetate activated VDR more potently than lithocholic acid, but its activity on FXR was weaker than that of chenodeoxycholic acid and comparable to that of lithocholic acid (Non-Patent Document 3).

Non-Patent Document 1: Expert Opin Ther Targets Vol. 10, 2006, pp. 735-748

Non-Patent Document 2: Science Vol. 296, 2002, pp. 1313-1316

Non-Patent Document 3: J Lipid Res Vol. 46, 2005, pp. 46-57

Non-Patent Document 4: Science Vol. 284, 1999, pp 1362-1365

Non-Patent Document 5: Biochem Biophys Res Commun Vol. 298, 2002, pp 714-719

DISCLOSURE OF THE INVENTION

Problems to be Solved by the Invention

An object of the present invention is to provide a VDR ligand which does not induce a blood calcium elevating action (hypercalcemia) which is an adverse reaction of vitamin D derivatives.

Means for Solving the Problems

The present inventors conducted extensive studies and acquired the following findings.

1. Lithocholic acid propionate activated VDR to the same extent as lithocholic acid acetate, but exhibited extremely weak potency on FXR. Lithocholic acid propionate exhibited extremely weak effects on a membrane receptor for bile acids or G protein-coupled bile acid receptor 1 (GPBAR1). Therefore, lithocholic acid propionate is a more selective VDR ligand (activating agent) than lithocholic acid and lithocholic acid acetate.

2. In experiments on mice, the effects of lithocholic acid propionate were compared to those of a vitamin D3 derivative (1α-hydroxyvitamin D3) at doses which induced the expression of the VDR target gene CYP24 in kidney to the same extent. 1α-Hydroxyvitamin D3 decreased the body weight of mice and induced hypercalcemia, but lithocholic acid propionate did not adversely affect the body weight or the blood calcium level.

3. Lithocholic acid propionate induced the differentiation markers for myeloid leukemia HL-60 and U937 cells.

The present invention was accomplished based on these findings.

The summary of the present invention is as follows.

(1) A composition comprising lithocholic acid propionate, a salt thereof, a solvate thereof, or a prodrug thereof.

(2) The composition according to the item (1) for activating a vitamin D receptor.

(3) The composition according to the item (1) or (2) which is used as a pharmaceutical.

(4) The composition according to the item (3) for preventing and/or treating diseases in which a vitamin D receptor is involved.

(5) The composition according to the item (3) or (4) for preventing and/or treating a disease selected from the group consisting of osteoporosis, malignant neoplasms, psoriasis vulgaris, autoimmune diseases, infectious diseases, and neurodegenerative diseases.

(6) A method for activating a vitamin D receptor, the method comprising treating a vitamin D receptor having cell, tissue, organ or animal individual with lithocholic acid propionate, a salt thereof, a solvate thereof, or a prodrug thereof.

(7) A method for preventing and/or treating diseases in which a vitamin D receptor is involved, the method comprising administering a subject with a pharmaceutically effective amount of lithocholic acid propionate, a salt thereof, a solvate thereof, or a prodrug thereof.

(8) Use of lithocholic acid propionate, a salt thereof, a solvate thereof, or a prodrug thereof, for activating a vitamin D receptor.

(9) Use of lithocholic acid propionate, a salt thereof, a solvate thereof, or a prodrug thereof, for the manufacture of a pharmaceutical for preventing and/or treating diseases in which a vitamin D receptor is involved.

Advantages of the Invention

Lithocholic acid propionate is effective as a VDR ligand (agonist).

The present specification encompasses the contents described in the specification and/or drawings of Japanese Patent Application No. 2007-147866, which is the basis of priority of the present application.

BRIEF DESCRIPTION OF THE DRAWINGS

FIG. 5 shows the effects of oral administration of lithocolic acid derivatives to mice. A shows body weight change. B shows plasma calcium level. C shows the mRNA expressions of Cyp24a1, calbindin $D_{9k}$, Trpv6 and Trpv5 in kidney. D shows the mRNA expressions of Cyp24a1, calbindin $D_{9k}$, and Trpv6 in intestinal mucosa. Mice were administered a vehicle control (Cont) (n=3), 1α(OH)D₃ (VD3) at 12.5 nmol/kg (n=3), lithocholic acid acetate (LCAa) at 0.7 mmol/kg (n=3) or 1 mmol/kg (n=6), or lithocholic acid propionate (LCAp) at 0.7 mmol/kg (n=3) or 1 mmol/kg (n=3) via gavage on days 0, 2, 4, 6, 8, and 10. Blood was collected from the tail on days 0, 2, 4, 6, and 8, and by heart puncture on day 12. Tissue mRNAs on day 12 were examined. * indicates $p<0.05$;  indicates $p<0.01$; * indicates $p<0.001$, compared with vehicle control.

BEST MODE FOR CARRYING OUT THE INVENTION

Hereinafter, the present invention will be described in detail.

The present invention provides a composition comprising lithocholic acid propionate, a salt thereof, a solvate thereof, or a prodrug thereof.

Lithocholic acid propionate is represented by the following structural formula.

[Formula 1]

Lithocholic acid propionate can be produced by the following method (1) or (2).

(1) A method wherein lithocholic acid and propionic anhydride are heated in an organic solvent (e.g., tetrahydrofuran) in the presence of an acid catalyst (e.g., $BF_3/Et_2O$); and (2) a method wherein the carboxyl group of a lithocholic acid is protected with a benzyl group or the like, and the alcohol moiety is reacted with a propionic acid chloride in pyridine to remove the protective group for the carboxylic acid.

Lithocholic acid propionate has a VDR activation effect. The VDR activation effect can be verified by the methods described in, for example, Science Vol. 284, 1999, pp 1362-1365 and Science Vol. 296, 2002, pp. 1313-1316. A VDR expression vector and a VDR-responsive reporter gene are introduced into a cell, which is then treated with a test compound (e.g., lithocholic acid propionate) and assayed for the reporter activity. VDR is determined to have been activated when the treated cell has an increased reporter activity compared to the untreated cell.

Lithocholic acid propionate was verified to cause the induction of the VDR target genes, but not to cause hypercalcemia (see Examples described later). Therefore, lithocholic acid propionate is useful as a VDR ligand which does not induce the blood calcium elevating action (hypercalcemia) which is the adverse effect of vitamin D derivatives.

Lithocholic acid propionate, when used as a pharmaceutical, may be rendered into a pharmaceutically acceptable salt by a common method. Examples of the salt of lithocholic acid propionate include mineral salts such as sodium, potassium, calcium salts; salts of ammonia and organic amines. Examples of the organic amines include tertiary amines such as triethylamine; secondary amines such as diethylamine; primary amines such as ethylamine; heterocyclic amines such as quinuclidine, pyridine, and the like.

Lithocholic acid propionate or a salt thereof may produce a solvate together with a solvent such as water, methanol, ethanol, or acetonitrile. The solvate may be a single component, or a mixture of two or more components.

Lithocholic acid propionate may be made in the form of a prodrug. The prodrug, after administered to a living body, is converted to a pharmaceutically active compound through enzymatic activities, metabolic hydrolysis, and the like. The prodrug may be any acid derivatives known in the art, and examples include esters produced by the reaction of lithocholic acid propionate with a suitable alcohol; amides produced by the reaction of lithocholic acid propionate with a suitable amine, alcohol analog 24 as a reduced form of the carboxy group, and the like.

Lithocholic acid propionate, a salt thereof, a solvate thereof and a prodrug thereof can be used as a drug to activate a vitamin D receptor. The drug can be used as a pharmaceutical or a reagent for experiments.

When used as a pharmaceutical, the drug can be used in the prevention and/or treatment of diseases in which a vitamin D receptor is involved. More specifically, the drug can be used in the prevention and/or treatment of osteoporosis, malignant neoplasms (e.g., myeloid leukemia, breast cancer, prostate cancer, colon cancer, etc.), psoriasis vulgaris, autoimmune diseases (e.g., chronic rheumatoid arthritis, systemic lupus erythematosus, etc.), infectious diseases (e.g., tuberculosis, etc.), neurodegenerative diseases (e.g., multiple sclerosis, etc.), etc.

When used as a pharmaceutical, lithocholic acid propionate, a salt thereof, a solvate thereof, or a prodrug thereof may be used singly, or may be mixed with an excipient or a carrier to formulate tablets, capsules, powders, granules, solutions or suspensions, syrups, aerosols, suppositories, injections, or the like. The excipient or carrier may be those which are routinely used in the art and are pharmaceutically acceptable, and the type and composition thereof are varied as necessary. For example, water or a vegetable oil is used as a liquid carrier. Solid carriers that may be used include saccharides such as lactose, saccharose, and glucose; starches such as potato starch and, corn starch; cellulose derivatives such as microcrystalline cellulose, etc. A lubricant such as magnesium stearate, a binder such as gelatin or hydroxypropyl cellulose, a disintegrator such as carboxymethyl cellulose, and the like may also be added. In addition, an antioxidant, a colorant, a flavor, a preservative, and the like may further be added. The drug may also be used in the form of a lyophilized product.

Lithocholic acid propionate, a salt thereof, a solvate thereof, or a prodrug thereof can be administered via various routes such as orally, transnasally, rectally, transdermally, subcutaneously, intravenously, or intramuscularly.

The content of lithocholic acid propionate, a salt thereof, a solvate thereof, or a prodrug thereof in pharmaceutical preparations varies in accordance with their type, but it is usually 1 to 100% by weight, preferably 50 to 100% by weight. For example, the content of lithocholic acid propionate, a salt thereof, a solvate thereof, or a prodrug thereof in solutions or suspensions is preferably 1 to 100% by weight in the pharmaceutical preparation. For capsules, tablets, granules and powders, the content of lithocholic acid propionate, a salt thereof, a solvate thereof, or a prodrug thereof is typically about 10 to about 100% by weight, preferably 50 to 100% by weight, in the pharmaceutical preparation, with the remainder being a carrier. The pharmaceutical may be prepared in unit dose formulations.

The dose of lithocholic acid propionate, a salt thereof, a solvate thereof, or a prodrug thereof may be any amount in which the expected preventive and/or therapeutic effects can be confirmed. The dose varies depending on the dosage form, administration route, the age and weight of the patient, the type and severity of the disease, but it is about 300 mg/kg per dose for an adult as calculated for the active ingredient, with the frequency of administration ranging from one to several times a day.

For use as reagents in experiments, cells, tissues, organs or animal individuals containing a vitamin D receptor may be treated with lithocholic acid propionate, a salt thereof, a solvate thereof, or a prodrug thereof to activate the vitamin D receptor. Lithocholic acid propionate, a salt thereof, a solvate thereof, or a prodrug thereof may be used in an amount effective to activate the vitamin D receptor. Examples of the vitamin D receptor-containing cells include the cells derived from the kidney, intestinal mucosa, bone marrow, bone, mammary gland, skin, and nerve. In addition to these naturally occurring cells, recombinant cells are also usable, such as those obtained by introducing a vitamin D receptor gene into human embryonic kidney-derived HEK293 cells; intestinal mucosa-derived HCT116 cells, SW480 cells, and Caco-2 cells; bone marrow-derived THP-1 cells, U937 cells, and HL60 cells; osteoblast cell-derived MG63 cells; mammary gland-derived MCF-7 cells; keratinocyte-derived HaCaT cells; nerve-derived SK-N-SH cells, liver-derived HepG2 cells, or the like. Examples of the vitamin D receptor-containing tissues and organs include the kidney, intestinal mucosa, bone marrow, lymphoid tissue, bone, mammary gland, skin, and nerve. Examples of the animal individual include mouse, rat, hamster, rabbit, and chicken. The vitamin D receptor activation can be verified by assaying the induced expression of a VDR target gene (e.g., CYP24, or the like).

Hereinafter, the present invention is more specifically described in reference to Examples, but the scope of the present invention is not limited thereto.

EXAMPLES

Example 1

[Formula 2]

A THF (4 mL) solution of lithocholic acid (376 mg, 1 mmol) and propionic anhydride (1.3 mL) was cooled to 0° C., $BF_3.Et_2O$ (32 µL, 0.25 mmol) was added thereto, and the mixture was heated under reflux for 15 hours. A saturated $NaHCO_3$ aqueous solution was added to the reaction mixture, which was then stirred at room temperature for 1 hour. The reaction mixture was extracted with ethyl acetate, the extract was washed with a saline solution, and dried with anhydrous $MgSO_4$ to evaporate the solvent. The residue was purified by column chromatography ($SiO_2$, 15 g, 15% ethyl acetate/hexane) to yield a propionate ester (346 mg, 80%). The ester was recrystallized with benzene/hexane to give a colorless crystal.

mp 152-153° C.

¹H NMR (δ) 0.64 (3H, s, H-18), 0.926 (3H, s, H-19), 0.92 (3H, d, J=5.5 Hz, H-21), 1.13 (3H, t, J=7.5 Hz, CH$_3$CH$_2$CO—), 2.27-2.36 (3H, m, H-23 & CH$_3$CH$_2$CO—), 2.36-2.44 (1H, m, H-23), 4.73 (1H, m, H-3).

¹³C NMR (d) 9.2, 12.0, 18.2, 20.8, 23.3, 24.1, 26.2, 26.6, 27.0, 28.0, 28.1, 30.7, 31.0, 32.2, 34.5, 35.0, 35.2, 35.7, 40.1, 40.3, 41.8, 42.7, 55.9, 56.4, 74.1, 174.1, 180.4.

MS m/z 432 (M⁺, 6.4), 358 (100), 343 (21), 304 (14), 257 (17), 230 (43), 215 (73).

Example 2

Figure 1:
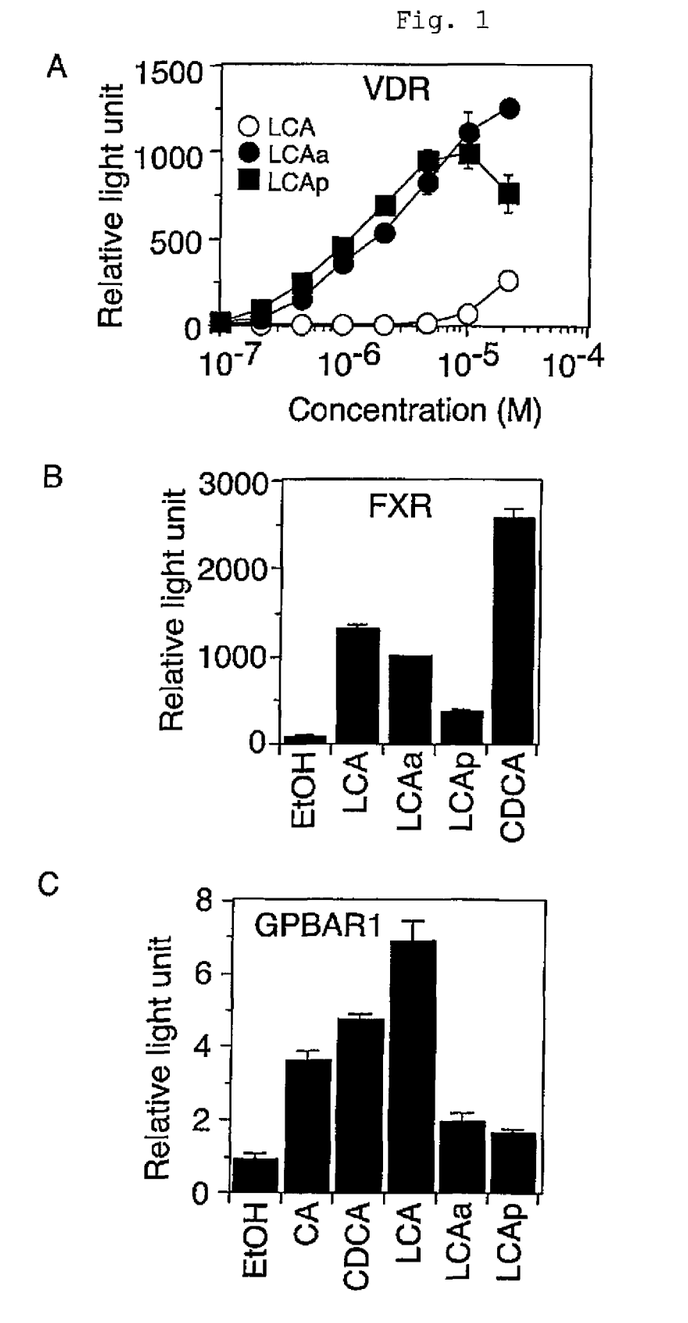
FIG. 1 shows the effects of lithocholic acid propionate on VDR, FXR and GPBAR1. LCA, lithocholic acid; LCAa, lithocholic acid acetate; LCAp, lithocholic acid propionate; EtOH, ethanol; CDCA, chenodeoxycholic acid; and CA, cholic acid. The compound concentrations used for the study were those shown in the figure for VDR, 18 μM for FXR, and 10 μM for GPBAR1.

In accordance with the methods described in the literature (Science Vol. 284, 1999, pp. 1362-1365; Science Vol. 296, 2002, pp. 1313-1316), lithocholic acid propionate was examined for the VDR activation potency. A CMX-GAL4-VDR expression vector (the CMX-GAL4-mRXRγ vector and CMX-hVDR vector donated by Professor Kazuhiko Umezono (deceased), Institute for Virus Research, Kyoto University were so processed as to replace the mRXRγ fragment with the corresponding hVDR ligand-binding region) and an MH100(UAS)×4-tk-LUC reporter vector (donated by Professor Kazuhiko Umezono (deceased), Institute for Virus Research, Kyoto University) were transfected in human embryonic kidney-derived HEK293 cells (obtained from an independent administrative institution, RIKEN BioResource Center) by the calcium phosphate coprecipitation assay. Eight hours after transfection, lithocholic acid propionate (prepared in Example 1) was added to the culture medium. Cells were solubilized 16 to 18 hours later, and evaluated for the luciferase activity. The results are shown in FIG. 1A. Lithocholic acid propionate was a more potent activator of VDR than lithocholic acid acetate.

Example 3

Figure 2:
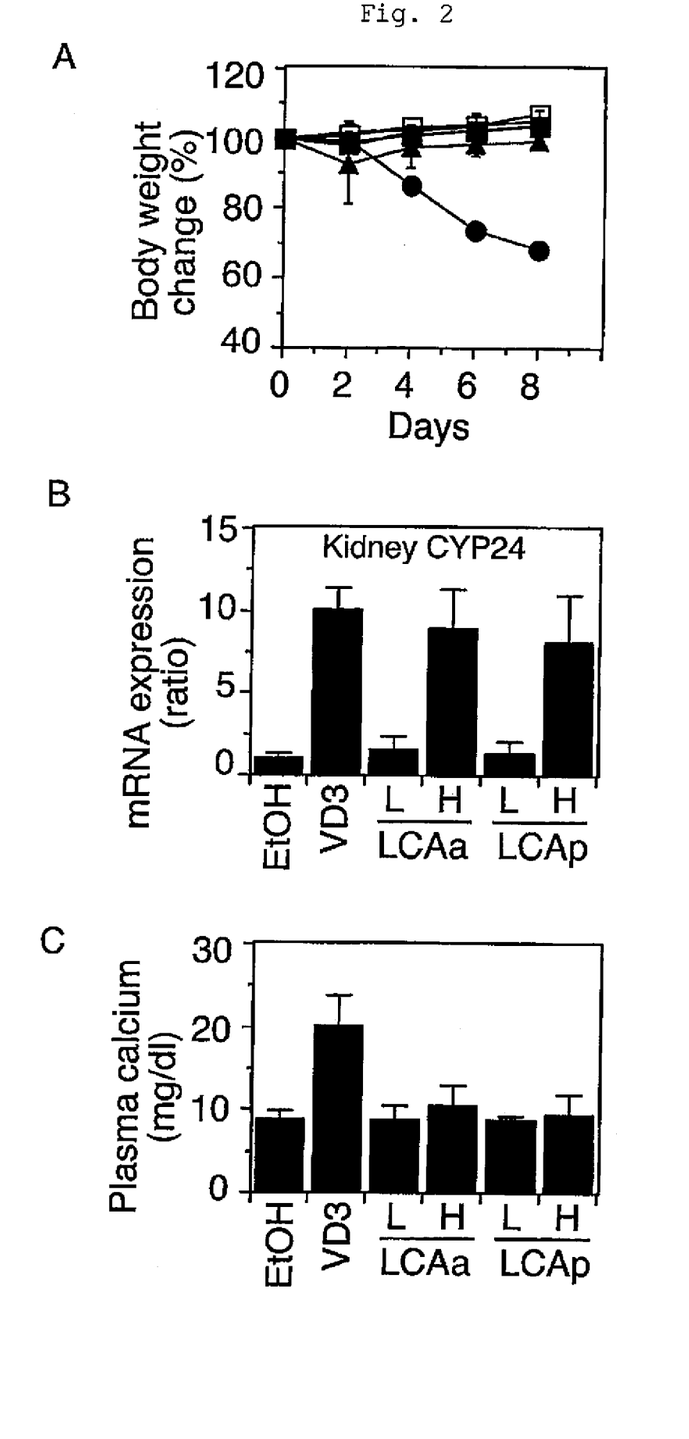
FIG. 2 shows the effects of lithocholic acid propionate in mice. A shows mice body weight change. B shows CYP24 mRNA expression in kidney. C shows plasma calcium level. 1α-hydroxyvitamin D3 was administered at 12.5 nmol/kg body weight (● in A, VD3 in B and C), lithocholic acid acetate was administered at 30 mg/kg body weight (Δ in A, L in B and C) or 300 mg/kg body weight (▲ in A, H in B and C), lithocholic acid propionate was administered at 30 mg/kg body weight (□ in L in B and C) or 300 mg/kg body weight (■ in A, H in B and C).

Lithocholic acid propionate was injected into animals to examine the plasma calcium level and the effect of inducing the expression of a VDR target gene in an organ. Male mice between 8 and 9 weeks of age (C57BL/6J, Charles River Laboratories Japan) were injected intraperitoneally with the compound dissolved in phosphate buffered saline every other day. On day 8, the plasma and the organ were collected. Plasma calcium was quantified by the o-cresolphthalein complexone method, and the expression of the VDR target gene CYP24 in kidney was assayed by the method described in the literature (J Lipid Res Vol. 46, 2005, pp. 46-57). Lithocholic acid propionate and lithocholic acid acetate induced the expression of the VDR target gene in the organ. The effect on the plasma calcium level was compared among 1α-hydroxyvitamin D3, lithocholic acid propionate, and lithocholic acid acetate at concentrations which induced the kidney CYP24 gene expression to the same extent. 1α-Hydroxyvitamin D3 induced hypercalcemia, but lithocholic acid propionate and lithocholic acid acetate did not change the calcium level (FIG. 2).

Example 4

Figure 3:
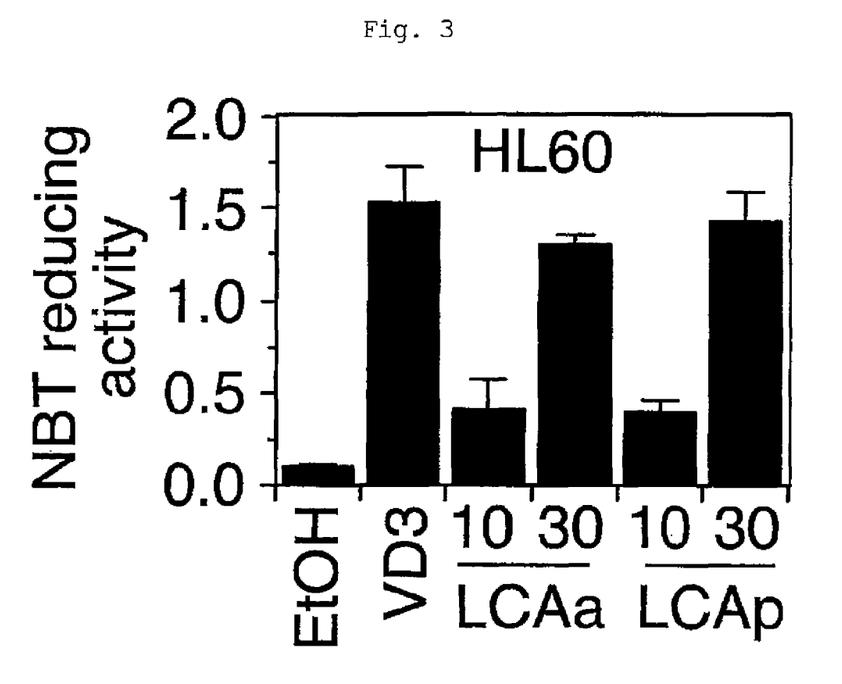
FIG. 3 shows the differentiation-inducing effect of lithocholic acid propionate on myeloid leukemia HL60 cells. The effects of lithocholic acid propionate at 10 μM and 30 μM were compared with those of 1,25-dihydroxyvitamin D3 at 100 nM and lithocholic acid acetate at 10 μM and 30 μM. EtOH, ethanol; VD3, 1,25-dihydroxyvitamin D3; LCAa, lithocholic acid acetate; and LCAp, lithocholic acid propionate.

In accordance with the method described in the literature (Biochem Pharmacol Vol. 57, 1999, pp. 521-529), lithocholic acid propionate was examined for the effect of inducing the differentiation of myeloid leukemia cells. Human myeloid leukemia HL60 cells (obtained from an independent administrative institution, RIKEN BioResource Center) were treated with the compound, and Nitro blue tetrazolium-reducing activity of the cells was determined 3 days later. Lithocholic acid propionate, similar to lithocholic acid acetate, induced the differentiation marker for HL60 cells weakly at 10 μM, but effectively at 30 μM (FIG. 3).

Example 5

Figure 4:
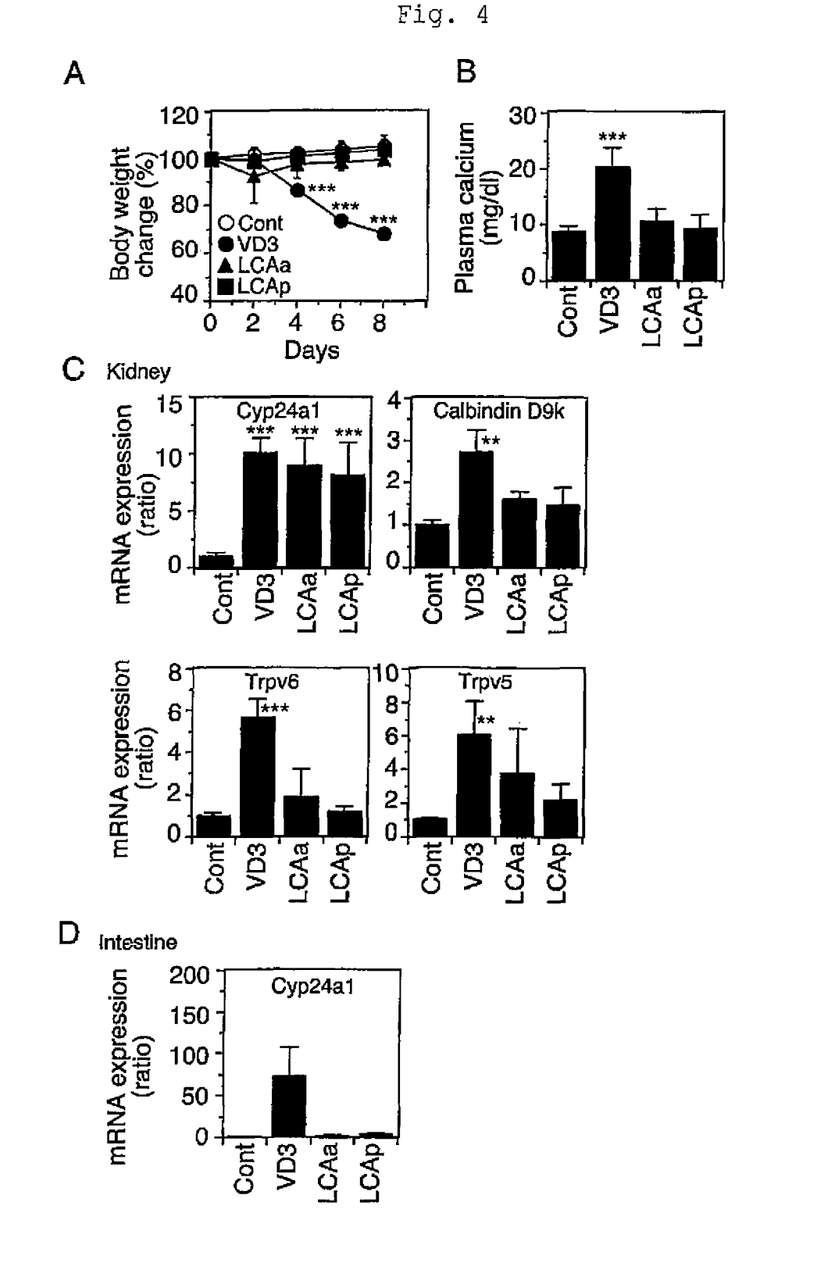
FIG. 4 shows the effects of intraperitoneal administration of lithocholic acid derivatives to mice. A shows mice body weight change. B shows plasma calcium level. C shows the mRNA expressions of Cyp24a1, calbindin $D_{9k}$, Trpv6, and Trpv5 in kidney. * indicates $p<0.05$;  indicates $p<0.01$; and * indicates $p<0.001$, compared with vehicle control. D shows the mRNA expression of Cyp24a1 in intestinal mucosa. p=0.190 (vehicle control vs. 1α(OH)D₃). Mice were administered a vehicle control (Cont) (n=3), 1α(OH)D₃ (VD3) at 12.5 mmol/kg (n=3), lithocholic acid acetate (LCAa) at 0.7 mmol/kg (n=3), or lithocholic acid propionate (LCAp) at 0.7 mmol/kg (n=3) via intraperitoneal injection on days 0, 2, 4, and 6. Blood was collected by heart puncture on day 8 and tissue mRNAs on day 8 were examined.

In order to examine the in vivo effects of lithocholic acid acetate and lithocholic acid propionate, mice (male mice between 8 and 9 weeks of age (C57BL/6J, Charles River Laboratories Japan)) were injected intraperitoneally with 1α-hydroxyvitamin D3 (1α(OH)D$_3$), lithocholic acid acetate or lithocholic acid propionate, as dissolved in phosphate buffered saline. 1α(OH)D$_3$ was rapidly converted to 1,25-dihydroxyvitamin D3 (1,25(OH)$_2$D$_3$) after injection but it was more effective than 1,25(OH)$_2$D$_3$ in increasing the survival time of the mice inoculated with leukemia cells. (Honma, Y., Hozumi, M., Abe, E., Konno, K., Fukushima, M., Hata, S., Nishii, Y., DeLuca, H. F., and Suda, T. 1983. 1,25-Dihydroxyvitamin D3 and 1.-hydroxyvitamin D3 prolong survival time of mice inoculated with myeloid leukemia cells. Proc Natl Acad Sci USA. 80: 201-204.) Intraperitoneal treatment of mice with 1α(OH)D$_3$ (12.5 nmol/kg) decreased their body weight (FIG. 4A) and increased the plasma calcium level (FIG. 4B). 1α(OH)D$_3$ effectively induced the expression of the kidney Cyp24a1, calbindin D$_{9k}$, Trpv6, and Trpv5 genes (FIG. 4C). 1α(OH)D$_3$ also induced the intestinal mucosa Cyp24a1 expression (FIG. 4D). Treatment of mice with lithocholic acid acetate (0.7 mmol/kg) or lithocholic acid propionate (0.7 mmol/kg) did not decrease their body weight (FIG. 4A). Importantly, lithocholic acid acetate (0.7 mmol/kg) and lithocholic acid propionate (0.7 mmol/kg) induced the expression of kidney Cyp24a1 as effectively as 1α(OH)D$_3$ (12.5 nmol/kg) (FIG. 4C), but these lithocholic acid derivatives did not change the plasma calcium level (FIG. 4B). The expressions of the intracellular calcium-binding protein calbindin D$_{9k}$ and the calcium transporters Trpv6 and Trpv5 were not effectively induced by the lithocholic acid derivatives. Lithocholic acid acetate and lithocholic acid propionate were not effective in inducing intestinal mucosa target gene expression (FIG. 4D).

Figure 5:
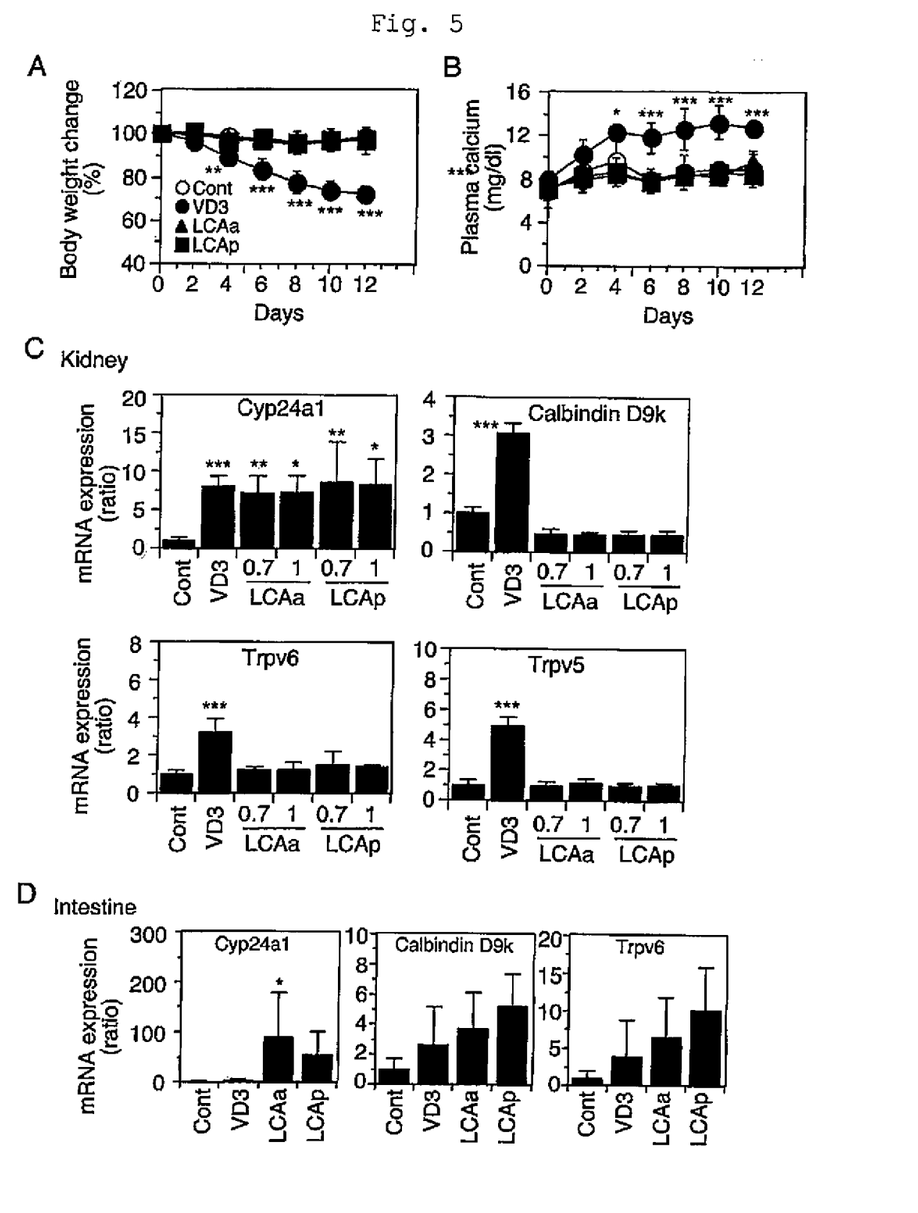

Next, the in vivo effects of orally administered lithocholic acid derivatives (dissolved in corn oil) were examined. Orally administered 1α(OH)D$_3$ decreased the body weight (FIG. 5A) and increased the plasma calcium level, but lithocholic acid acetate (1 mmol/kg) or lithocholic acid propionate (1 mmol/kg) did not affect the body weight or plasma calcium (FIG. 5B). Lithocholic acid acetate (0.7 mmol/kg and 1 mmol/kg) and lithocholic acid propionate (0.7 mmol/kg and 1 mmol/kg) induced the kidney Cyp24a1 expression as effectively as 1α(OH)D$_3$ (12.5 nmol/kg) (FIG. 5C). The expression of kidney calbindin D$_{9k}$ was not induced by lithocholic acid acetate or lithocholic acid propionate treatment. Unlike 1α(OH)D$_3$, the lithocholic acid derivatives did not increase the Trpv6 and Trpv5 expressions. The expression of intestinal mucosa Cyp24a1 was not increased after a 10 day oral administration of 1α(OH)D$_3$ (FIG. 5D). Since the expression was not observed after a 1 day single oral dose (data not shown), the lack of induction during the 10 day administration may be due to the adaptation mechanism(s) reported previously. (Lemay, J., Demers, C., Hendy, G. N., Delvin, E. E., and Gascon-Barre, M. 1995. Expression of the 1, 25-dihydroxyvitamin D3-24-hydroxylase gene in rat intestine: response to calcium, vitamin D3 and calcitriol administration in vivo. J Bone Miner Res. 10: 1148-1157.) The effects of the lithocholic acid derivatives which were observed with respect to intestinal mucosa Cyp24a1 expression were modest. Therefore, lithocholic acid acetate and lithocholic acid propionate can activate a vitamin D receptor (VDR) in vivo without the toxic effects of weight loss and hypercalcemia.

Pharmaceutical Preparation Example 1

Thirty grams of lithocholic acid propionate, 140 g of micro crystalline cellulose, 100 g of lactose, 15 g of calcium cellulose glycolate, 10 g of hydroxypropylcellulose, and 30 ml of purified water were added to a kneader and kneaded for 5 minutes by a common method. After kneading, the obtained product was sieved through a 10-mesh screen and dried in a drier at 50° C. After drying, the product was granulated and 5 g of magnesium stearate was added thereto. After mixing for 1 minute, tablet-pressing was performed to make tablets each having a weight of about 100 mg and a diameter of 6.5 mm. Each tablet contained 1.0 mg of lithocholic acid propionate.

All publications, patents, and patent applications cited herein should be incorporated in its entirety in this specification by reference.

INDUSTRIAL APPLICABILITY

The present invention can be used for prevention and/or treatment of diseases in which a vitamin D receptor is involved, specifically, osteoporosis, malignant neoplasms (e.g., myeloid leukemia, breast cancer, prostate cancer, colon cancer, etc.), psoriasis vulgaris, autoimmune diseases (e.g., chronic rheumatoid arthritis, systemic lupus erythematosus, etc.), infectious diseases (e.g., tuberculosis, etc.), neurodegenerative diseases (e.g., multiple sclerosis, etc.), and the like.

The invention claimed is:

1. A method of activating a vitamin D receptor without inducing a blood calcium elevation comprising:
    administering to a subject a pharmaceutically effective amount of lithocholic acid propionate, or a salt thereof
    wherein the administration results in reduced activation of farnesoid X receptor (FXR) compared to lithocholic acid acetate.

2. A method according to claim 1,
    wherein the pharmaceutically effective amount in capsule, tablet, granule, or powder form is 10 to 100% of lithocholic acid propionate or a salt thereof, by weight with the remainder being a carrier.

3. A method according to claim 1,
    wherein the pharmaceutically effective amount in capsule, tablet, granule, or powder form is 50 to 100% of lithocholic acid propionate or a salt thereof, by weight with the remainder being a carrier.

4. A method according to claim 1, wherein the pharmaceutically effective amount is given to an adult in a dosage of about 300 mg/kg per dose.

5. A method of activating a vitamin D receptor without inducing a blood calcium elevation comprising:
    administering to a subject a pharmaceutically effective amount of lithocholic acid propionate, or a salt thereof,
    wherein the effective amount of lithocholic acid propionate is administered to a subject having a disease selected from the group consisting of osteoporosis, psoriasis vulgaris, and autoimmune disease, and
    the administration results in reduced activation of farnesoid X receptor (FXR) compared to lithocholic acid acetate.

6. A method according to claim 5, wherein the pharmaceutically effective amount in solution or suspension is 1 to 100% of lithocholic acid propionate or a salt thereof by weight.

7. A method according to claim 5,
    wherein the pharmaceutically effective amount in capsule, tablet, granule, or powder form is 10 to 100% of lithocholic acid propionate or a salt thereof by weight with the remainder being a carrier.

8. A method according to claim 5,
    wherein the pharmaceutically effective amount in capsule, tablet, granule, or powder form is 50 to 100% of lithocholic acid propionate or a salt thereof by weight with the remainder being a carrier.

9. A method according to claim 5, wherein the pharmaceutically effective amount is given to an adult in a dosage of about 300 mg/kg per dose.

10. A method of treating malignant neoplasm selected from the group consisting of myeloid leukemia, breast cancer, prostate cancer, and colon cancer without inducing a blood calcium elevation comprising:
    administering to a subject a pharmaceutically effective amount of lithocholic acid propionate, or a salt thereof, wherein administration results in reduced activation of farnesoid X receptor (FXR) compared to lithocholic acid acetate.

11. A method according to claim 10, wherein the pharmaceutically effective amount in solution or suspension is 1 to 100% of lithocholic acid propionate or a salt thereof by weight.

12. A method according to claim 10,
    wherein the pharmaceutically effective amount in capsule, tablet, granule, or powder form is 10 to 100% of lithocholic acid propionate or a salt thereof by weight with the remainder being a carrier.

13. A method according to claim 10,
    wherein the pharmaceutically effective amount in capsule, tablet, granule, or powder form is 50 to 100% of lithocholic acid propionate or a salt thereof by weight with the remainder being a carrier.

14. A method according to claim 10, wherein the pharmaceutically effective amount is given to an adult in a dosage of about 300 mg/kg per dose.

15. The method according to claim 1, wherein the pharmaceutically effective amount in solution or suspension is 1 to 100% of lithocholic acid propionate or a salt thereof by weight.

* * * * *